US00PP20489P3

(12) United States Plant Patent
Rader

(10) Patent No.: US PP20,489 P3
(45) Date of Patent: Nov. 17, 2009

(54) ***JUNIPERUS CHINESIS* PLANT NAMED 'NEDSYELO'**

(50) Latin Name: *Juniperus chinensis*
Varietal Denomination: Nedsyelo

(76) Inventor: Ned D. Rader, 18580 Chambers Rd., Amanda, OH (US) 43102-9417

( * ) Notice: Subject to any disclaimer, the term of this patent is extended or adjusted under 35 U.S.C. 154(b) by 37 days.

(21) Appl. No.: 12/002,680

(22) Filed: Dec. 18, 2007

(65) Prior Publication Data

US 2009/0158481 P1 Jun. 18, 2009

(51) Int. Cl.
*A01H 7/00* (2006.01)

(52) U.S. Cl. ..... Plt./214

(58) Field of Classification Search ..... Plt./214
See application file for complete search history.

*Primary Examiner*—Susan B McCormick Ewoldt
(74) *Attorney, Agent, or Firm*—Frank H. Foster; Kremblas, Foster, Phillips & Pollick

(57) ABSTRACT

A new plant variety of *Juniperus chinensis* that is distinguished from its parent and all other varieties of *Juniperus chinensis* by having bright yellow-green needles combined with unusually slow growth and compact habit.

4 Drawing Sheets

Figure 3:
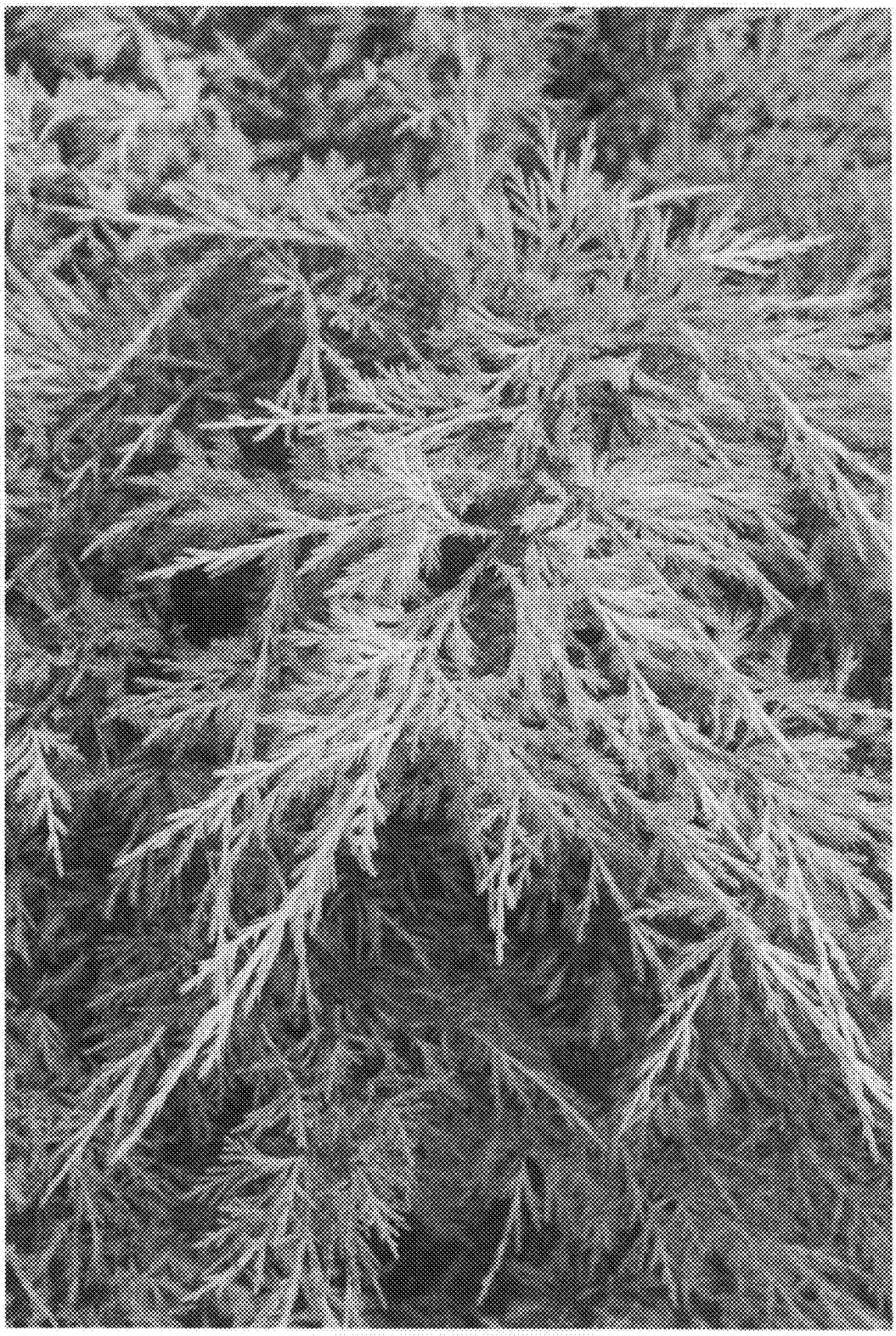

Latin name: *Juniperus chinensis* .

Varietal denomination: 'Nedsyelo'.

BACKGROUND OF THE INVENTION

The present invention relates to a new and distinct variety of *Juniperus chinensis* which occurred as a branch sport mutation on a mature cultivated specimen of *Juniperus chinensis* 'Pfizteriana' (not patented) in a foundation landscape planting near Amanda, Ohio U.S. and discovered by Mr. Ned D. Rader of Amanda, Ohio. The varietal denomination of the new variety is 'Nedsyelo'. The genus *Juniperus* is included within the family Cupressaceae which comprises about 60 species in the northern hemisphere from the Polar Regions to high elevations in the tropics. Junipers range in habit from groundcovers to small trees. Leaves arranged oppositely or in whorls are either scale-like (adult) or awl shaped or acicular leaves (uvenile). Junipers are generally dioecious with male sporophylls numbering 3–7, yellow. Seed cones appear fleshy or berry-like, glaucous, consisting of 3–8 united scales.

'Nedsyelo' Juniper was first asexually reproduced by Mr. Rader at Amanda, Ohio in the summer of 1991 when he took cuttings from the sport branch of the parent plant, which branch was showing the yellow foliage of 'Nedsyelo' Juniper. In the initial propagation of this plant, summer cuttings were used. They were cut to a length of 3–5", dipped in Indolebutyric acid rooting hormone (IBA), stuck in a combination sand/styrofoam rooting medium and placed under a mist system which misted every 10 minutes for 6–10 seconds. They were left under the mist system until they were rooted, then kept in the greenhouse over the first winter. Subsequent propagation was done as winter cuttings. All propagation of 'Nedsyelo' Juniper remains true to the original branch sport mutation.

'Nedsyelo' Juniper is easily reproduced from winter hardwood cuttings taken in November through January, averaging a success rate of 60–90%. The rooted cuttings grow off quickly in 2½" pots and can be transplanted into 1 gallon containers and finished out at the end of 1 or 2 growing seasons.

To date, there has been no burning of foliage, no insect or disease infestation, drought, or cold hardiness effect on any of the 100–200 plants that are growing at Amanda, Ohio for 10–15 years. These plants have not suffered any dieback from winter cold temperatures even though they have been through drought conditions and temperature lows of −15 degrees Fahrenheit. The plants have never received any irrigation when planted in field conditions. No fruit or flowers have been noticed on the older plants to date. The only fragrance produced is when the leaves are crushed or cut. Deer do not bother the plants even though deer are present in substantial numbers.

Plant shows hardiness, surviving stressful conditions of extreme drought and extreme high and low temperatures without burning of foliage. Even though the plant is vigorous, it does not spend its energy in becoming large, rather it remains compact (about half the size of other yellow junipers such as 'Saybrook Gold' Juniper—U.S. Plant Pat. No. 5,014) and symmetrically shaped over time, requiring little maintenance. I measured 3 specimens of 'Saybrook Gold' Juniper which were growing at an arboretum in Newark, Ohio. These plants were growing in a spaced out, arboretum-like area. These plants measured six feet high by eleven feet wide (19 years old); six feet high by sixteen feet wide (25 years old); eight feet high by thirteen feet wide (20 years old). These are considerably larger than the oldest plants of 'Nedsyelo' Juniper, which is four feet high by six feet wide (17 years old).

SUMMARY OF THE INVENTION

The new variety was discovered as a spontaneous branch sport mutation on a mature specimen of *Juniperus chinensis* 'Pfitzeriana' growing at a residential site located at Amanda, Ohio. The parent has subsequently died and has been removed. The new variety differs from its parent in having bright yellow outer needles and creamy yellow-green interior needles. The new variety also exhibits an unusually slow growth rate and maintains a distinctively compact habit. The asexual reproduction of the new variety in Amanda, Ohio by cutting propagation has confirmed that the distinctive qualities of the new variety are stable and reproduced true to type in successive generations of asexual propagation.

COMPARISON WITH PARENT AND KNOWN CULTIVARS

The parent plant is a *Juniperus chinensis* 'Pfitzeriana'. It is a large, 10–15' wide and 8–10' tall conifer shrub with glaucous (bluish) scale-like and juvenile glaucous foliage on stout arm-like branches ascending at acute angles with drooping tips. 'Nedsyelo' is distinguished from its parent and other varieties of Chinese Juniper by its bright yellow needles which maintain this bright color year-around and by its slow growth and compact habit.

'Nedsyelo' Juniper is more compact growing with bright yellow new growth, starting in spring and lasting throughout the following winter into the next spring, so that the first year growth remains yellow through the winter until the beginning of the second spring, when new yellow growth begins again and the second year wood turns orange-tan, but has new yellow growth on it also. Shaded foliage is mostly light green with slight blue-green (glaucous) mixed in. New growth shows the yellow color best in sunlight. New growth is bright lemon yellow in sunlight and stays yellow throughout the first winter. New growth is a moderate 3–6" as compared to Saybrook Gold Juniper, which is faster growing. 'Nedsyelo' Juniper is dwarfer than Saybrook Gold Juniper. 'Nedsyelo' Juniper at 15 years is 7' wide×4' tall, whereas Saybrook Gold Juniper is 15' wide×9' tall at 20 years. 'Nedsyelo' Juniper does not show any tip blight whereas Saybrook Gold Juniper shows severe tip blight in rainy years at Wooster, Ohio. Additional observations are as follows:

1. *Juniperus* c. 'Saybrook Gold' (U.S. Plant Pat. No. 5,014) (2–3'H×6'W—Similar to 'Nedsyelo' but showing old gold color in winter; not as lemon yellow as 'Nedsyelo'. Plants that were 6' H×12' W showed lots of tip blight;
2. 'Gold Coast' Juniper (not patented) (3'H×4–5'W)—Similar to 'Nedsyelo' but not as yellow in spring;
3. 'Gold Sovereign' Juniper (not patented) (18–24" H×2½–3' W)—Smaller than 'Nedsyelo';
4. 'Sea of Gold' Juniper (3' H×4'W)—Very similar to 'Nedsyelo'; 'Nedsyelo' shows yellow color on new growth for a longer period;
5. 'Gold Lace' Juniper U.S. Plant Pat. No. 8,202 (3–4'H×5–6'W)—'Nedsyelo' shows more yellow growth in spring;
6. 'Aorangi Gold' Juniper (not patented)—Turns old gold in winter; 'Nedsyelo' is more lemon gold in winter.

BRIEF DESCRIPTION OF ILLUSTRATIONS

The accompanying photographs show a specimen of the new cultivar as true to color as is reasonably possible to make in an illustration of this character.

FIG. 1 Mature 'Nedsyelo' Juniper taken in late summer, showing compact habit (10 years old).

FIG. 2 Sample of 3" pot transplanted to 1 gallon container, showing size 6 months after transplant (18 months old).

FIG. 3 Closeup of 'Nedsyelo' Juniper in early summer, showing bright yellow new growth on 11 year old plant.

Figure 4:
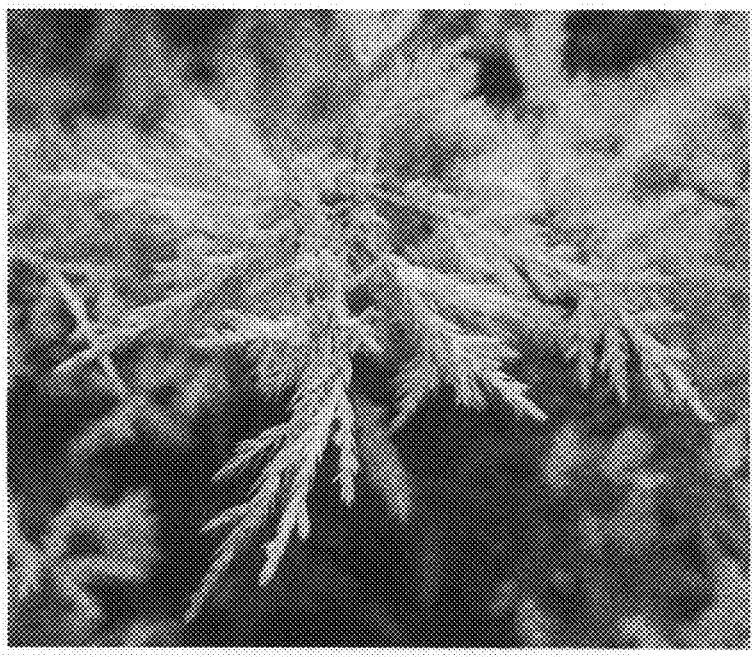

FIG. 4 Closeup of 'Nedsyelo' Juniper showing bright yellow color of tip growth on mature plant (11 years old).

Figure 5:
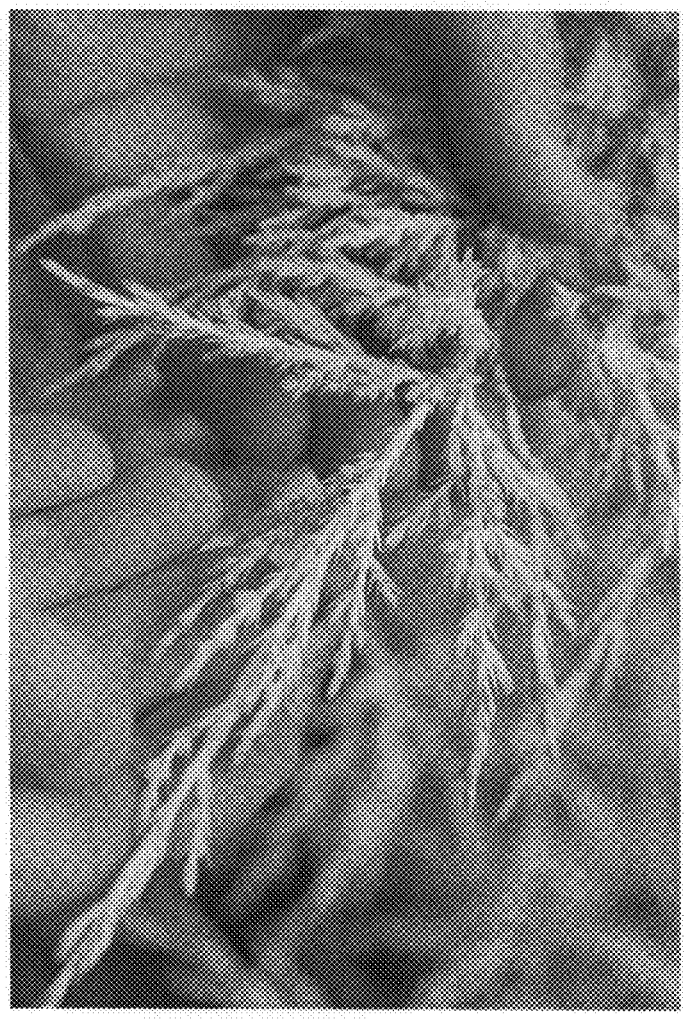

FIG. 5 Closeup of 'Nedsyelo' Juniper showing second year orange stem, first year bright yellow new growth and yellow green hues of interior needles on new growth (11 years old).

Figure 6:
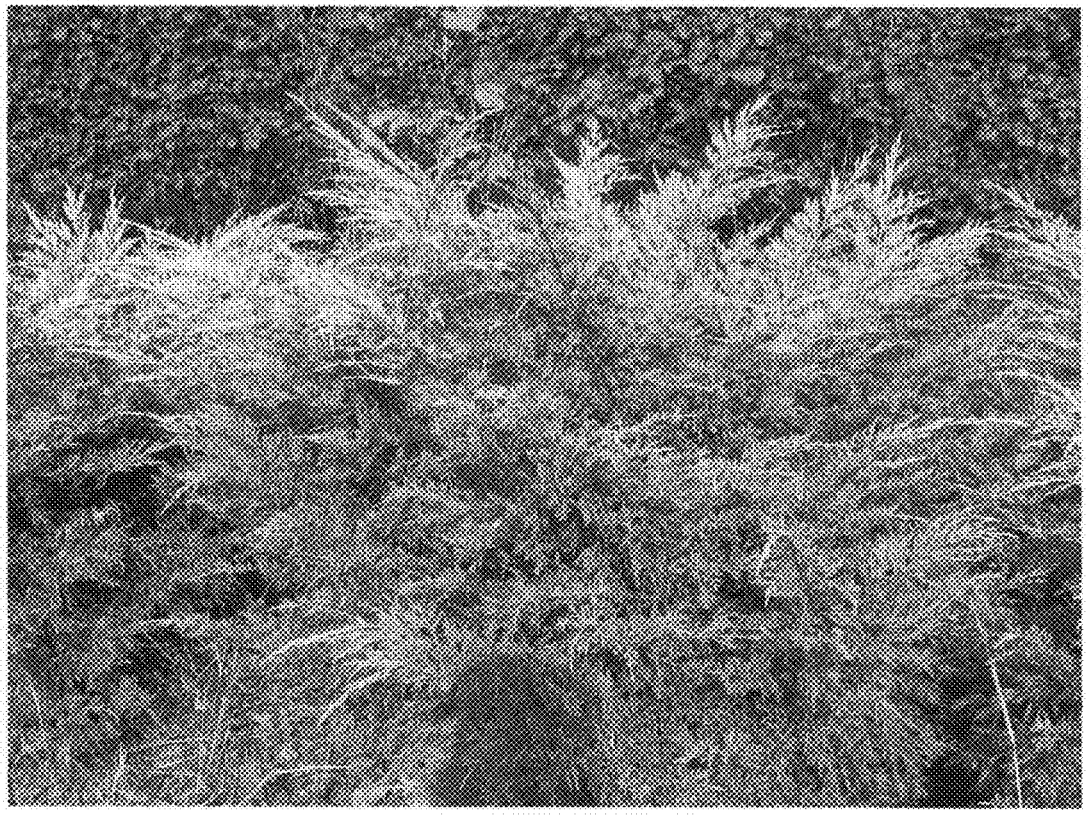

FIG. 6 is a photo taken in November showing sustained yellow color on one year old growth (11 years old).

DETAILED DESCRIPTION OF THE NEW VARIETY

'Nedsyelo' Juniper has been observed under a wide variety of environmental and cultural conditions. The following observations and descriptions are of plants (10 years old) growing at Amanda, Ohio. In these descriptions, color references are based on The Royal Horticultural Society Colour Chart and color terminology used in the descriptions herein refers to plate numbers in this R.H.S. Color Chart. Phenotypic expression may vary with light intensity and environmental conditions.

Classification:

*Botanical.*—*Juniperus chinensis* (L).

*Parentage.*—Original plant: *Juniperus chinensis* 'Pfitzeriana'.

*Propagation.*—Cuttings.

Plant:

*Typical size.*—1.45 meters tall by 2.0 meters wide.

*Observed size.*—Ranging from 0.7 meters tall by 1.2 meters wide on 10 yr old plants to 1.45 meters tall by 2.0 meters high on 15 year old plants.

*Habit.*—Mounded to flat topped spreading wider than tall; densely branched, compact.

Branches:

*Lateral branches.*—5–10.

*Size.*—Diameter: Base diameter on 15 yr plants is 254 mm, 76.2 mm on 10 yr old plants 3$^{rd}$ rd year old shoots — 5 mm in diameter, apical shoots — 3 mm diameter.

*Color.*—200D on oldest wood, 3$^{rd}$ year old shoots grey-orange group 177A. Apical shoots grayed-yellow 162C.

*Texture.*—Glabrous on young shoots, exfoliating on older bark.

Leaf:

*Shape.*—Juvenile needles temate and acicular, adult needles flattened and scale like.

*Size.*—Adult needles 7–20 mm long, juvenile needles 4–9 mm long.

*Arrangement.*—Opposite.

*Margins.*—Entire.

*Texture/substance.*—Shrub medium coarse textured, juvenile foliage prickly, adult foliage scale-like.

Description of foliage: Young needles bright yellow intensifying somewhat in winter but holding good color in summer (RHS yellow group ranging from 3C to 6A). Interior needles dark green splashed with yellow margins (RHS yellow group ranging from 151A to 151B).

Width of variegation.—3–7 mm

*Young foliage.*—Upper and lower sides lemon yellow 7A older needles merging to yellow-green 151B Mature interior foliage is yellow-green 151B merging to green 141C.

Transition zone between margins and central coloration: Yellow-green 151 C

Mature foliage central: Yellow group 141C

Petioles: 2–10 mm long adult, 4–7 mm long juvenile coloration-interior green group 148C, apical yellow-green group 151 C.

Internodes: 2–10 mm adult, 3–4 mm juvenile

Hardiness: USDA zone 4

Vigor: Slow, 4–6" new growth per year.

Pests/diseases:Bbag worms (*Thyridopteryx emphemeraeformis*), spruce spider mite (*Oligonydnis ununguis*), shoot blight (*Phomopsis juniperova*)

Inflorescence: From observation over a 17-year period no fruit has ever been noticed on any plants nor have any staminate cones been observed on 'Nedsyelo' Juniper.

I claim:

1. A new and distinct variety of *Juniperus chinensis* plant named 'Nedsyelo' substantially as illustrated and described herein.

* * * * *

Fig. 1
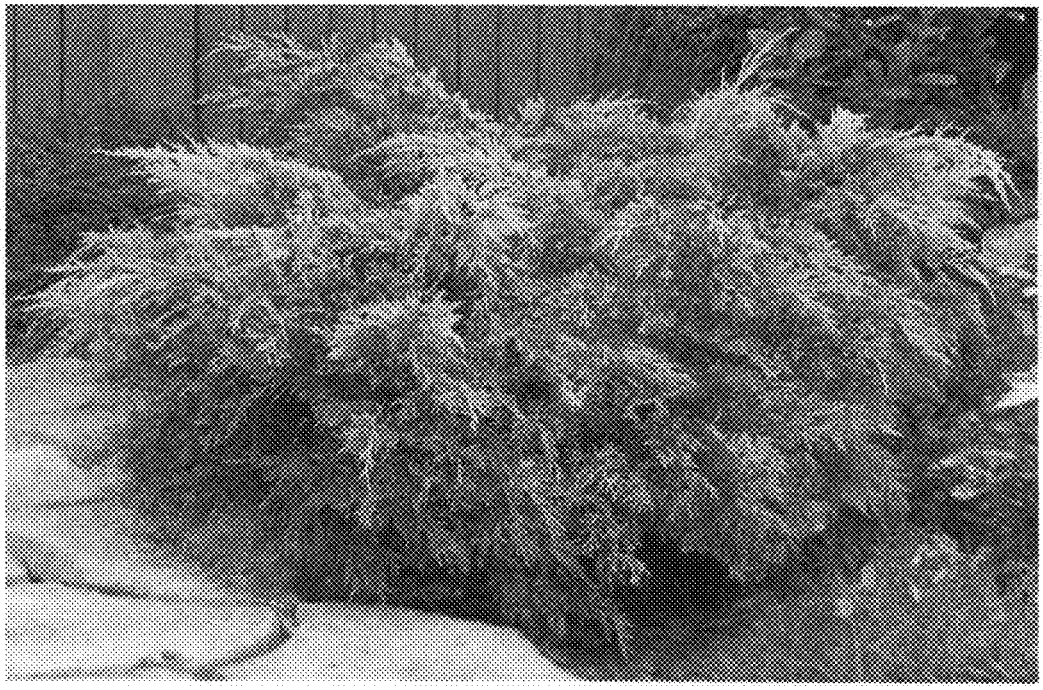
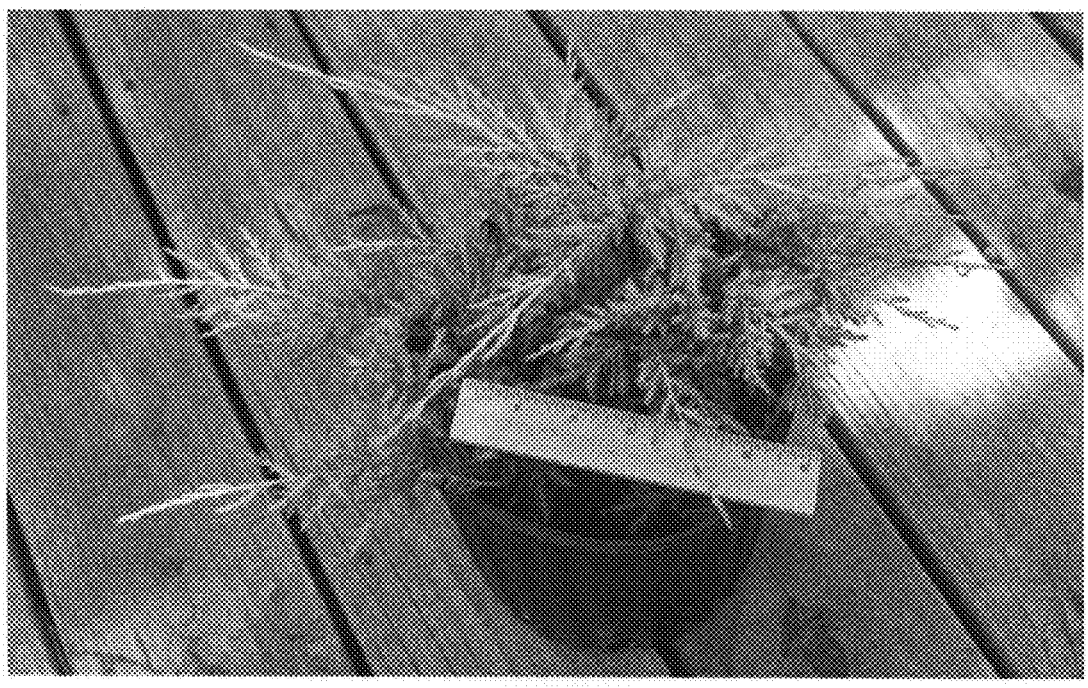
Fig. 2